United States Patent [19]

Bridoux et al.

[11] 4,157,665

[45] Jun. 12, 1979

[54] FORMATION OF ACOUSTICAL IMAGES

[75] Inventors: Edouard Bridoux, Maing; Christian D. Bruneel, Marly; Roger J. Torguet; Bertrand Nongaillard, both of Saint-Saulve, all of France

[73] Assignee: Agence Nationale de Valorisation de la Recherche (ANVAR), Neuilly Sur Seine, France

[21] Appl. No.: 839,979

[22] Filed: Oct. 6, 1977

[30] Foreign Application Priority Data

Oct. 11, 1976 [FR] France .................................. 76 30476

[51] Int. Cl.$^2$ ............................................ G01N 29/04
[52] U.S. Cl. ....................................... 73/607; 128/660; 340/5 MP
[58] Field of Search ................. 73/603, 606, 607, 625, 73/626, 628, 641; 340/5 MP, 5 H, 9; 128/2 V, 2.05 Z

[56] References Cited

U.S. PATENT DOCUMENTS

| | | | |
|---|---|---|---|
| 3,778,756 | 12/1973 | Houston et al. | 73/607 X |
| 3,895,525 | 7/1975 | Eichelberger et al. | 73/607 |
| 3,918,297 | 11/1975 | Rocha | 73/607 |

Primary Examiner—Richard C. Queisser
Assistant Examiner—John P. Beauchamp
Attorney, Agent, or Firm—Daniel M. Rosen

[57] ABSTRACT

A device for forming acoustical images comprises an ultrasonic source, a linear array of first receiving transducers for receiving the echoes from a target illuminated by a source. The signals from the linear array of first receiving transducers are processed by a system comprising an oscillator at a frequency higher than that of the source, and, for each said receiving transducers, a mixer, a filter for separating the components of the beating frequency and a transmitting transducer.

6 Claims, 5 Drawing Figures

FORMATION OF ACOUSTICAL IMAGES

The present invention relates to methods and devices for forming an acoustic image, useful notably for exploring a part or an organ in depth, that is to say to carry out B echography.

Numerous B echography devices are already known. They generally include an array or a mosaic of transducer-receivers arranged so as to receive the ultrasonic waves reflected by a part or an organ illuminated by an ultrasonic source which provides pulses, which source can moreover be constituted by the array or the mosaic operating alternately in transmission and in reception. This solution has limitations. In particular, exploration point by point or by a group of transducers does not enable a sufficiently rapid rate of images to be achieved in numerous cases and notably in the medical field. In addition, this method does not permit a satisfactory image to be obtained: in fact, and through its very principle, such a device only collects the shadow of the discontinuities reflecting the ultrasonic waves.

Besides these sounding devices there is known a submarine sounding installation of the sonar type, comprising a two-dimensional matrix of transducer-receivers, each transducer being connected to a data-processing channel. If the image rate can thus be increased, the second drawback mentioned above subsists in its entirety.

It is an object of the present invention to provide improved methods and devices for the formation of an acoustic image, it is a more particular object to provide a device which delivers a real image while embodying a relatively simple electronic system.

To this end, the invention proposes notably a method according to which: the amplitude of the acoustic field pulsed at a frequency $\Omega/2\pi$ deriving from a target is sampled by means of an array of first transducer-receivers, which array has one or two dimensions; on the sampled signals a phase inversion is carried out by electrical beat formation between said signals and a reference signal with $\Omega/2\pi$ frequency, $\Omega$ being greater than $\omega$, then isolation of frequency $\pi(\Omega-\omega)/2$; a real image creating acoustic field is reconstructed by applying the signals at frequency $\frac{1}{2}\pi(\Omega-\omega)$ to an array of transducer-emitters, with one of two dimensions as the case may be.

This method finds a particularly important application in the medical field; it permits in fact a sufficiently high image rate to be achieved to observe in real time the operation of organs moving at high speed, such as cardiac valves. However, its applications are not limited to the medical field, nor even to that where the organ or the part to be explored is illuminated by an external source. For example, the invention also permits the determination of the distribution of the ultrasonic emission foci in a part or an organ, foci due for example to the relaxation of stresses in a loaded part, with an image rate sufficient to permit dynamic testing.

The real image can notably be detected by means of an array, with one or two dimensions as the case may be, of second transducer-receivers placed in the focal plane of the array of transducer-emitters.

A device according to another aspect of the invention comprises a pulsed source of ultrasonic waves at frequency $\omega/2\pi$, an array of n first transducer-receivers distributed in at least one predetermined direction, for receiving the echoes received from a target irradiated by the source, and means for processing of the signals supplied by said first transducer-receivers, characterised in that said treatment means comprise: a source of electrical supply at frequency $\Omega/2\pi$; n channels, each associated with one of the first transducer-receivers and each comprising a mixer between a signal of the first corresponding transducer-receiver and the signal at frequency $\Omega/2\pi$, an isolating filter for the component with frequency $\frac{1}{2}\pi(\Omega-\omega)$, a transducer-emitter belonging to an array of n distributed transducers; and an array of second transducer-receivers placed in the focal plane of the array of transducer-emitters and associated with a viewing device.

By modifying either $\Omega$, or $\omega$, it is possible to modify the focussing distance, which gives great flexibility of employment to the device.

The invention will be better understood on reading the description which follows of devices which constitute thereof particular embodiments given by way of non-limiting example. The description refers to the drawings which accompany it, in which.

Figure 1:
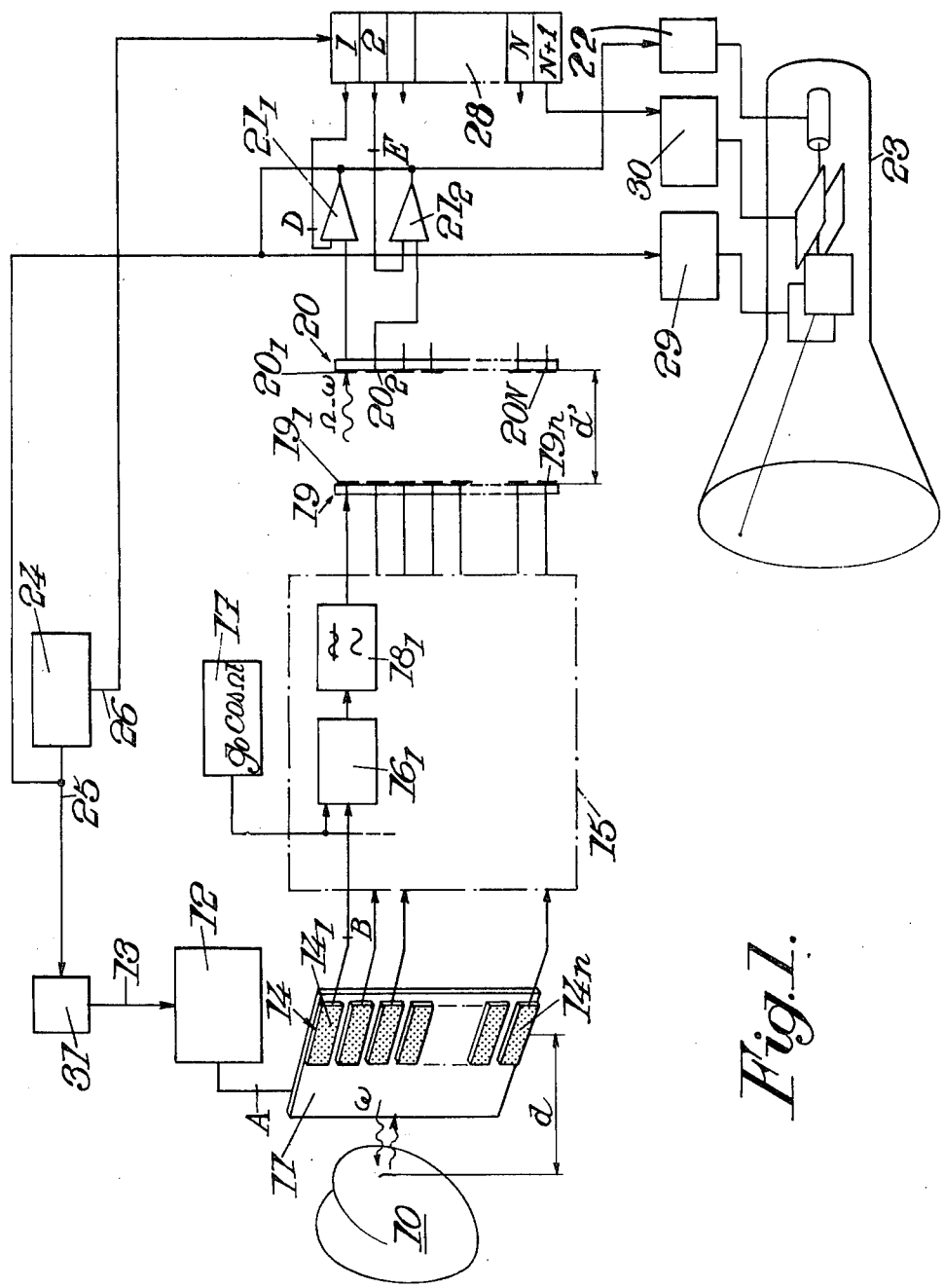
FIG. 1 is a schematic diagram of a first device.

The device shown diagramatically in FIG. 1 is intended for B echography. It will be assumed, for clarity, that it relates to a device for exploration of the cardiac muscle 10.

The device comprises a source of ultrasonic illumination, which will be for example constituted by a piezoelectric ceramic generator applied against the skin. This generator 11 is driven by an oscillator 12 including a control input 13. As long as the signal is applied to the control input 13, the oscillator 12 supplies the ultrasonic generator 11 with an energizing electrical signal of the form $F_O \cos \omega t$. In general, a frequency $\omega/2\pi$ will be selected, comprised, in conventional manner, between 2 and 4 MHz.

The echoes returned by the heart 10 are collected by an array 14 of first elementary transducer-receivers $14_1$, ... $14_n$. In the embodiment illustrated in FIG. 1, the n transducers are distributed linearly and are constituted by an array adjacent to the source 11. This array can, in entirely conventional manner, be constituted by a piezoelectric ceramic covered, on one surface, with a conductive layer connected to ground or to a biasing voltage and, on the other surface, with conductive strips each defining an elementary transducer. Each of these strips is connected, through a corresponding electrical lead, to one of n channels of an electronic processing system 15. Each channel includes successively an amplifier (not shown) for increasing the voltage of the output signal. As a general rule, it suffices for the amplifier to have a gain of the order of 80 db. The amplified signal is applied to one of the inputs of a mixer, $16_1$ for example, of which the other input receives the output signal from a generator 17 of pulses having an angular frequency $\Omega$ with $\Omega > \omega$. If for example the frequency $\omega/2\pi$ is 3 MHz, the generator 17 would generally be given a frequency comprised between 5 and 8 MHz. This generator does not need to be stabilised accurately in frequency. Mixers such as $16_1$ can be of conventional type and constituted, for example, by ring modulators.

If the signal collected by elementary transducer-receiver $14_1$ is denoted by $f_O \cos(\omega - \phi)$ and the reference signal supplied by the generator 17 by $g_O \cos \Omega t$, the mixer $16_1$ provides at its output a beat signal given by the formula:

$$(f_O g_O/2) \cos[(\Omega-\omega)t+\phi]+(g_O f_O/2) \cos[(\Omega+\omega)t-\phi] \qquad (1)$$

It is seen that this output signal resulting from the beat includes a term at angular frequency $\Omega-\omega$ whose phase is reversed with respect to that of the signal supplied by the transducer $14_1$ and whose amplitude is directly proportional to that of the signal from the transducer. This phase inversion enables a real image to be reconstituted. For this, each channel associated with a transducer contains means enabling the pulsation term $\Omega - \gtrless$ to be isolated. In the embodiment illustrated in FIG. 1, these means are constituted by a lowpass filter $18_1$ whose cut-off frequency is less than $(\Omega+\omega)/2\pi$. It can be a conventional passive filter, insuring an attenuation of 6 db per octave, eliminating the frequency $(\Omega+\omega)/2\pi$ and the residual components at the input frequencies.

The electronic system 15 drives an array 19 of n elementary transducers $19_1, \ldots 19_n$, each elementary transducer receiving the output signal arriving from the corresponding mixer, if necessary through a filter. The array 19 can have a constitution similar to that of the array 14. It is never necessary however for the two arrays to be identical, or even to have the same shape. In particular, if the array 14 is rectilinear, the array 19 can have an incurved shape as well as rectilinear.

If the transducers $19_1$ to $19_n$ are of the type eliminating high frequencies, which is particularly the case of transducers using a piezo-electric ceramic, it is often possible to dispense with filters 18.

A simple calculation shows that transducer-emitters $19_1$ to $19_n$ cause the formation of a real image at a predetermined distance d' for which their contributions occur in phase.

In fact, if the distance between the array 14 of first transducer-receivers and an echo source discontinuity is denoted by d, the phase distribution along the array, from the point of the latter which faces the echo source is as follows:

$$\phi = 2\pi x^2/\lambda d$$

x being the distance from the point of the array which faces the echo source.

The contributions of the different elementary emitter transducers of the array 19 corresponding to this echo source are in phase at distance d' such that:

$$2\pi x'^2/\lambda' d' = 2\pi x^2/\lambda d$$

$\lambda$ and $\lambda'$ being the wave lengths in the media traversed by the ultrasonic waves respectively between the echo source and the array 14 and from the array 19.

If the array 19 is immersed in water, $\lambda$ and $\lambda'$ will be substantially equal in the case of medical imagery. However in certain cases it may be preferable to apply the array 19 to one surface of a part of a solid material. It is then possible to cause the transducers of the array 19 to operate in transverse waves, for which the speed of sound is of the same order as the speed of longitudinal waves in liquids. It is possible notably to utilise as a solid material a metal, such as brass or copper, permitting the use of wide band transducers.

The ratio between d' and d will be a function of the beat frequency $\Omega - \omega$ and of the ratio of the spacing between transducers in the arrays 14 and 19.

The device also includes an array 20 of second elementary transducer-receivers. These transducers are placed at distance d' from the array 19. These second transducer-receivers $20_1 \ldots 20_N$ can be equal in number to that of the elementary transducers of the arrays 14 and 19, but this condition is in no way indispensable. In fact, the transducers of the array 20 have simply the purpose of sampling the acoustic field created by the array 19.

Each second transducer-receiver, $20_1$ for example, drives the input of an analog gate, $21_1$ for example. The signal could if necessary be detected before the input of the gate. The outputs from all gates are connected, in the embodiment illustrated, to the circuit 22 controlling the brightness of a spot on the viewing screen (Wehnelt of a cathode ray tube screen 23 in FIG. 1).

Figure 2:
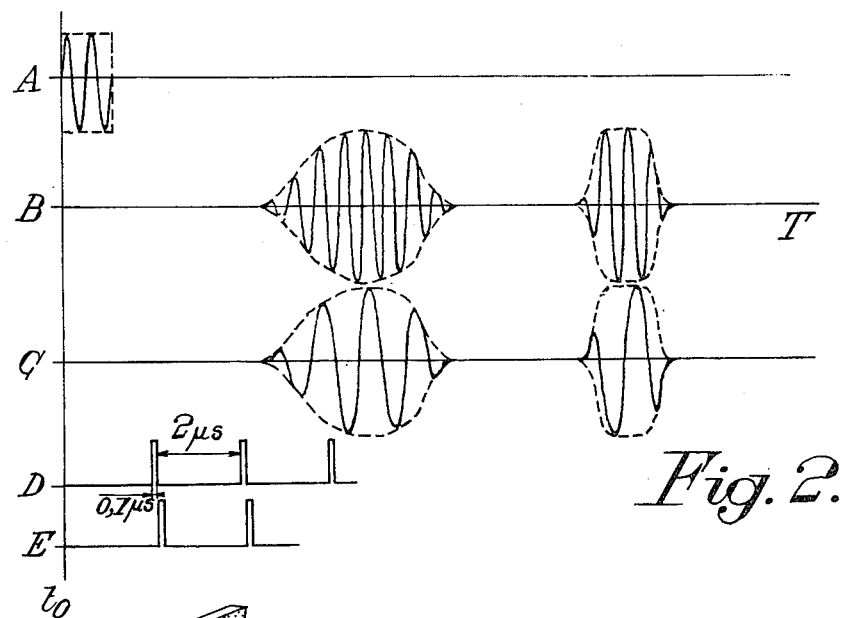
FIG. 2 is a synoptic diagram showing, in very simplified manner, the shape of signals which appear at various points of the device of FIG. 1, FIGS. 3, 4 and 5 are schematic diagrams showing various possible configurations of the array of the second transducer-receivers.

The device includes sequence circuits shown diagramatically in the form of a time base 24 including an output 25 supplying signals for starting the cycles (at 2 kHz for example) and an output 26 supplying clock pulses (at 10 MHz for example) to a shift register device 28 with N positions. Each output of this shift register, $28_1$ for example, controls the opening of one of the analog gates, $21_1$ for example. In FIG. 2 examples are presented of output signals from the shift register (the line D indicating the signal applied at $21_1$ and the line E then applied at $21_2$). The output 25 is connected also to the horizontal sweep control circuit 29 (image sweep) of the cathode screen. The vertical sweep is synchronous with the sampling effected on the various channels. The circuit 30 is driven either by the first output pulse from the shift register $28_1$ or by a (N+1)th position provided for this purpose (and illustrated in the Figure) or by any other signal synchronous with the sampling cycles.

The operation of the device which has thus been discribed is shown diagramatically in FIG. 2, which corresponds to the case of an image repetition rate which, in principle, can go up to 5 KHz, using arrays 14, 19 and 20 of forty transducers. By way of indication, it can be noted that satisfactory images are obtained by using an array 14 whose transducers are distributed with a spacing of 2 mm.

At the moment $t_O$ of the beginning of the cycle, the time base 24 emits, at its output 25, a signal which is applied to a monostable element 31. The latter applies to the oscillator 12 a triggering signal of predetermined duration. For a definition in depth of 1.5 mm in the human body, it is possible for example to adopt a duration of emission of 2 $\mu$s. A signal of the shape indicated diagramatically on line A is applied to the ultrasonic wave source 11.

The various discontinuities encountered by the ultrasonic beam (notably front and rear surfaces of the heart, valves, etc.) send back echoes which are collected by the transducers of the array 14. For example, there is collected at the output of the transducer $14_1$ a signal which can have a general shape as indicated at B. A reset circuit, not shown, will be provided to cut off the output amplifiers from the first transducer-receivers $14_1 \ldots 14_n$ at the end of a suitable time interval T, of 200 $\mu$s for example.

After beating and filtering, the transducer $19_1$ receives a signal of the type indicated at C. Comparable signals are applied to the other transducers of the array 19.

The acoustic field created by the transducers $19_1, \ldots 19_n$ is collected by the linear array 20 of second transducer-receivers $20_1 \ldots, 20_n$. At the beginning of the vertical sweep saw-tooth of the CRT screen the shift register 28 opens the gate $21_1$ and the brightness of the spot is controlled by the amplitude of the signal detected by the second transducer-receiver $20_1$. At the next moment, at the end of 0.1 μs in the case of a clock signal of 10 MHz, the spot will be moved over the screen and the brightness will be controlled by the signal received by the transducer $20_2$ and so on up to transducer $20_N$. Then the saw-tooth is reset to zero and another cycle starts, giving the image of a line slightly more spaced from the array of first transducer-receivers. The time interval between the formation of two successive lines is equal to 2 μs, namely a distance of 1.5 mm in the human body. The period of formation of an image corresponding to a depth of 15 cm equals 200 μs; it is preferable not to commence a new image immediately, otherwise deep echoes of an image would risk being confused with the first echoes of the following image.

If the number of transducers is very high, it is obviously possible to sample, during each elementary cycle of 2 μs, only one predetermined group of sampler-lockers, one half or one quarter for example.

The invention is capable of numerous modifications, in particular, the sampling system may have any constitution enabling the acoustic field of the array of transducers 19 to be explored. In addition, the transducers can be grouped in patterns having a different constitution from those which have been described above. Some additional examples, not to be considered as exclusive in any way, will now be described.

Figure 3:
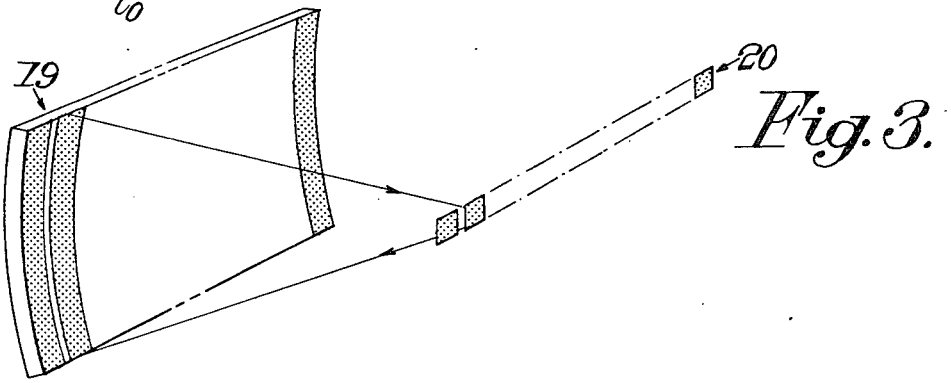

To insure geometric focussing and hence to increase the amplitude of the acoustic field, one or other of the arrays of transducers may be constituted of elementary transducers having a considerable development in the direction perpendicular to the array, the transducers having the form of cylindrical segments. FIG. 3 shows an array of elementary transducer-emitters 19 of this type, the curvature of the transducers being provided to cause focussing in the plane of the real image. Under these conditions, the array of second elementary transducer-receivers 20 can have a small development in the transverse direction.

Figure 4:
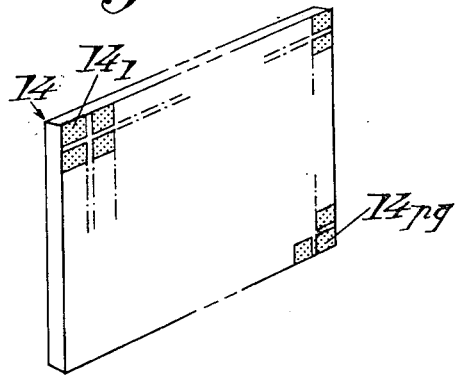

Instead of an array, it is possible, to effect two dimension scanning to use a mosaic 14 of n transducers with p lines and q columns, of the type shown diagramatically in FIG. 4. The transducers are not necessarily distributed in a rectangular matrix: any other shape of distribution may be adopted to correspond to particular cases, the elementary transducers being distributed with a regular or, on the contrary, variable spacing.

Figure 5:
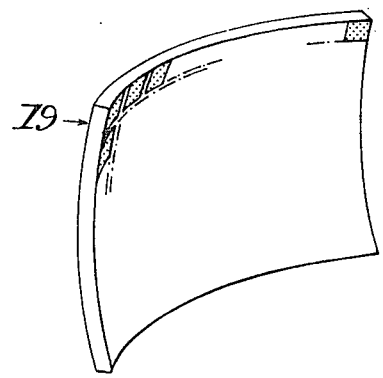

In case of a two-dimensional array, it is possible also to give the mosaic of transducers a shape which is no longer flat, but a shape of cylindrical or spherical segments. FIG. 5 shows, by way of example, such a distribution for the mosaic of elementary transducer-emitters 19.

The invention is obviously in no way limited to the particular embodiments which have been shown and described by way of example and it must be understood that the scope of the present patent extends to all modifications remaining within the field of equivalence.

We claim:

1. A method for forming an image of an acoustic wave field originating from a target irradiated with pulses of acoustic energy at a frequency $\omega/2\pi$, comprising the steps of sampling said field by first receiving transducers distributed in an at least one-dimensional array, beating the electrical signals from said first receiving transducers with a reference signal at frequency $\Omega/2\pi$, $\Omega$ being greater than $\omega$; electrically isolating and recovering the beat frequency signals at frequency $(\Omega-\omega)/2\pi$ to invert the phase of the sampled signals and applying the signals at frequency $(\Omega-\omega)/2\pi$ to an at least one dimensional array of transmitting transducers for reconstructing a real image creating acoustic field.

2. A method according to claim 1 comprising the further step of sampling said real image by means of an area of second receiving transducers distributed in at least one dimension and placed in the focusing plane of said area of transmitting transducers.

3. Device for forming image of an acoustic wave field, having: a pulsed source of ultrasonic waves of frequency $\omega/2\pi$; an array of n first receiving transducers distributed along at least one predetermined direction (n being a predetermined integer) for receiving the echoes reflected from a target irradiated by the source; means for processing the signals supplied by said first transducer-receivers, wherein said processing means comprise: a source of electrical signals at frequency $\Omega/2\pi$; n processing channels, each operatively associated with one of the first receiving transducers and each including a mixer having a first input connected to receive signals from a corresponding first receiving transducer and another input connected to receive a signal at frequency $\Omega/2\pi$ from the electrical source, an electrical filter for isolating and recovering the component at frequency $(\Omega-\omega)2\pi$ from the input signal of the mixer, a transmitting transducer belonging to an array of n distributed transducers; and an array of second receiving transducers placed in the focussing plane of the array of transmitting transducers and operatively associated with display means.

4. Device according to claim 3, further comprising means for modifying one at least of the frequency $\omega/2\pi$ of the ultrasonic waves supplied by the source and the frequency $\Omega/2\pi$ of the signal supplied by the electrical supply source, so as to modify the focussing distance.

5. Device according to claim 3, wherein said first receiving transducers are distributed along a linear array.

6. Device according to claim 3, wherein the receiving transducers are distributed according to a mosaic of n=p.q elementary transducers, p and q being the numbers of transducers in rows and columns of the mosaic.

* * * * *